①② United States Patent
Goldstein et al.

(10) Patent No.: US 7,318,998 B2
(45) Date of Patent: Jan. 15, 2008

(54) TISSUE DECELLULARIZATION

(75) Inventors: Steven Goldstein, Atlanta, GA (US);
Kirby S. Black, Acworth, GA (US)

(73) Assignee: Cryolife, Inc., Kennesaw, GA (US)

( * ) Notice: Subject to any disclaimer, the term of this patent is extended or adjusted under 35 U.S.C. 154(b) by 330 days.

(21) Appl. No.: 10/394,576

(22) Filed: Mar. 24, 2003

(65) Prior Publication Data

US 2003/0228692 A1 Dec. 11, 2003

Related U.S. Application Data

(63) Continuation of application No. 09/735,522, filed on Dec. 14, 2000, now abandoned, which is a continuation of application No. 08/838,852, filed on Apr. 11, 1997, now abandoned.

(51) Int. Cl.
*A01N 1/02* (2006.01)

(52) U.S. Cl. ............... 435/1.3; 435/270; 435/378; 623/11.11; 623/66.1; 623/915; 623/916; 623/918; 128/898

(58) Field of Classification Search ............... None
See application file for complete search history.

(56) References Cited

U.S. PATENT DOCUMENTS 4,776,853 A * 10/1988 Klement et al. ............ 8/94.11
5,632,778 A * 5/1997 Goldstein ................... 424/423
5,843,182 A * 12/1998 Goldstein ................... 128/898

* cited by examiner

*Primary Examiner*—David Redding
(74) *Attorney, Agent, or Firm*—Nixon & Vanderhye P.C.

(57) ABSTRACT

The present invention relates, in general, to tissue decellularization and, in particular to a method of treating tissues, for example, heart valves, tendons and ligaments, so as to render them acellular and thereby limit mineralization and/or immunoreactivity upon implementation in vivo.

12 Claims, 4 Drawing Sheets

US007318998B2

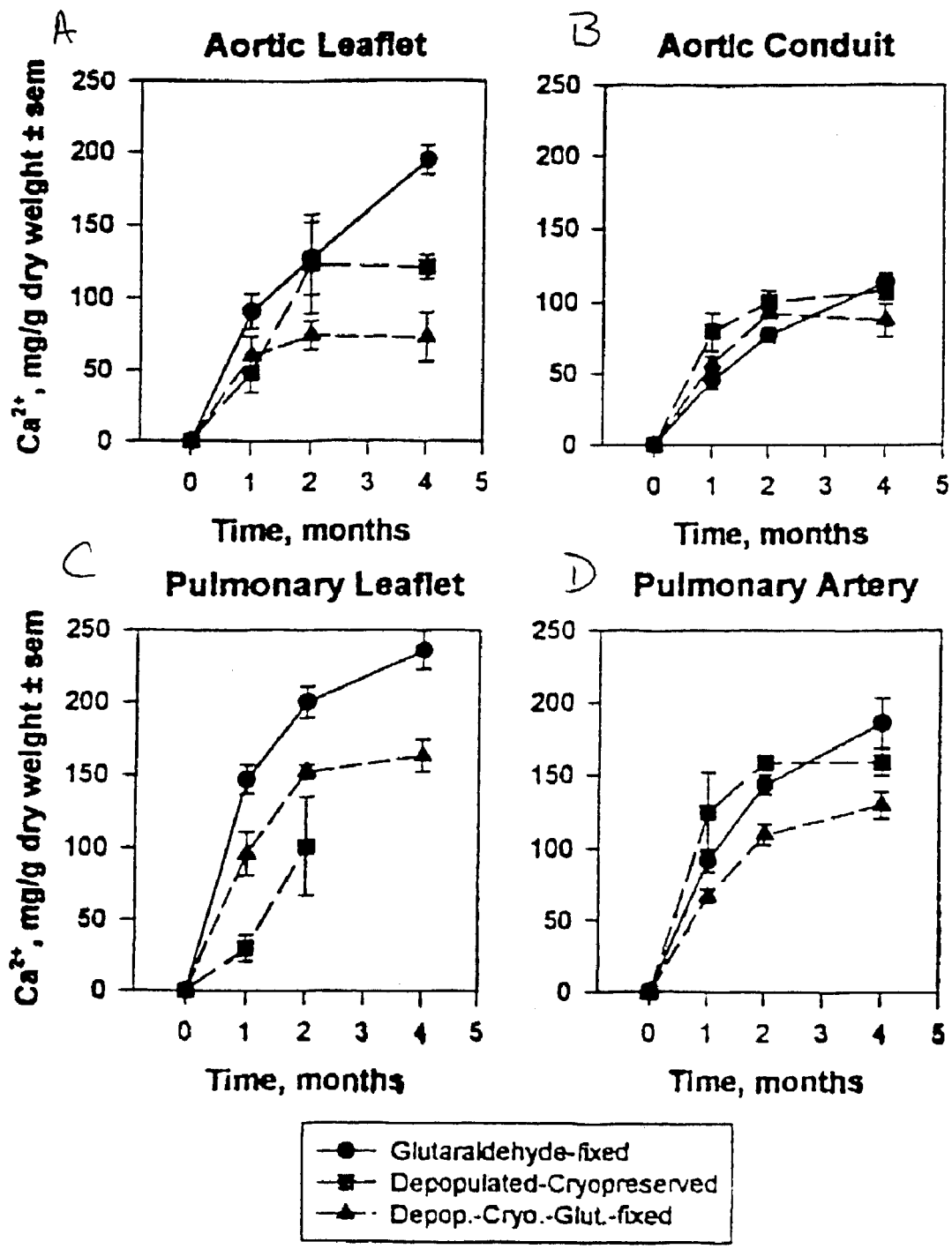

TISSUE DECELLULARIZATION

This application is a continuation of application Ser. No. 09/735,522, filed Dec. 14, 2000, now abandoned, which is a continuation of application Ser. No. 08/838,852, filed Apr. 11, 1997, now abandoned, the entire contents of which are hereby incorporated by reference in this application.

TECHNICAL FIELD

The present invention relates, in general, to tissue decellularization and, in particular to a method of treating tissues, for example, heart valves, ligaments and tendons, so as to render them acellular and thereby limit mineralization and/or immuncreactivity upon implantation in vivo.

BACKGROUND

Cardiac valve disorders can be serious and in fact are often fatal. Treatment may require replacement of the valve with a prosthetic valve—mechanical or bioprosthetic. Bioprosthetic valves typically include a leaflet portion and a vascular conduit portion, both generally of a biological material, and possibly a stent.

While bioprosthetic valves have a number of advantages over mechanical valves, including a lower risk of complications resulting from thrombus formation, they are associated with a higher risk of mineralization. This increased risk significantly limits the durability of the replacement valve. The present invention provides a method of rendering tissues, including heart valves, resistant to mineralization while preserving biomechanical properties of the tissue. The present invention also provides a method of reducing immunoreactivity of transplanted tissues which are not fixed by chemical or physical means, or combinations thereof, prior to implantation.

OBJECT AND SUMMARY OF THE INVENTION

It is a general object of the invention to provide a method treating tissue so as to limit mineralization and/or immunoreactivity post implantation.

It is another object of the invention to provide a method of decellularizing a tissue and thereby enhancing its durability and/or reducing its immunoreactivity.

It is a further object of the invention to provide a tissue, for example, a heart valve bioprosthesis, that retains mechanical integrity, is resistant to calcification and is characterized by reduced immunoreactivity upon implantation.

The foregoing objects are met by the present invention which provides a method of effecting decellularization of tissues, including heart valve tissues (eg leaflets and valve associated vascular conduit). The method comprises contacting the tissue to be decellularized with a hypotonic solution under conditions such that cell lysis occurs, and subsequently subjecting the tissue to nuclease treatment under conditions such that the tissue is rendered histologically acellular.

Further objects and advantages of the present invention will be clear from the description that follows.

BRIEF DESCRIPTION OF THE DRAWINGS

FIGS. 4A, B, C and D show the effect of decellularization on calcification of porcine heart aortic and pulmonary heart valve tissues.

DETAILED DESCRIPTION OF THE INVENTION

Figure 1:
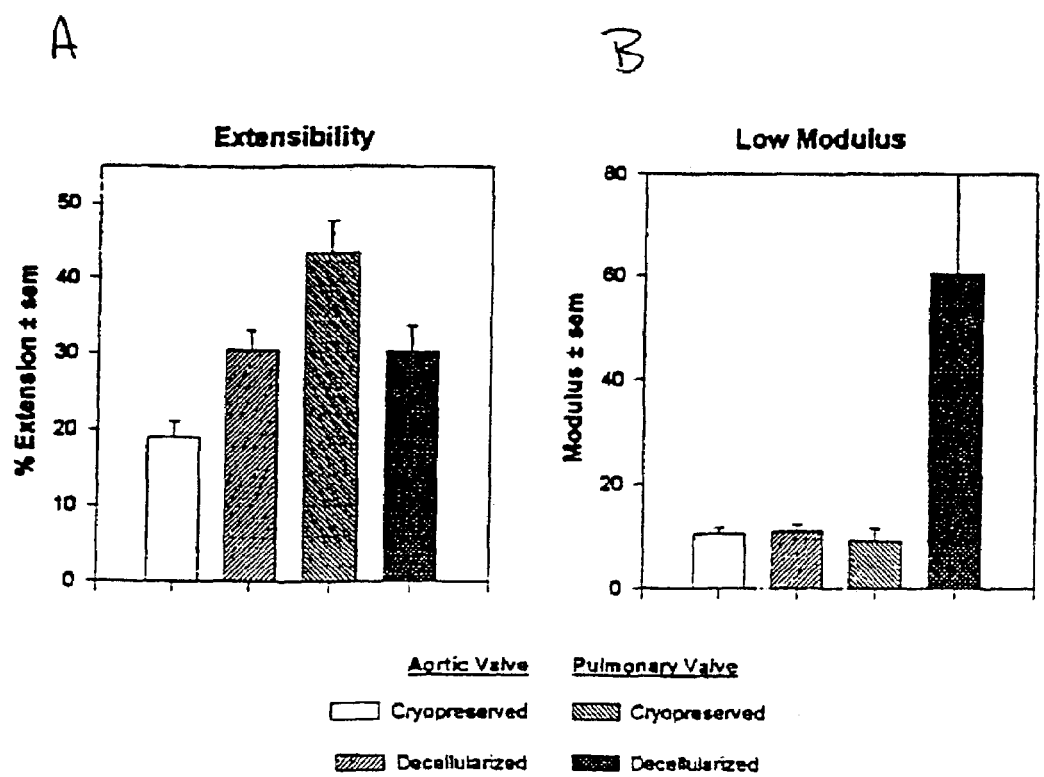
FIGS. 1A and B show the effect of decellularization on the extensibility of and elastic modulus of aortic and pulmonary leaflets.

The present invention relates, in one embodiment, to a method of rendering a biological tissue acellular. The method comprises exposing the tissue to a hypotonic solution under conditions such that cell lysis results, and subjecting the resulting tissue to nuclease treatment so as to remove nucleic acids and associated phosphorous-containing groups which may bind calcium. Nuclease treatment effectively stops cell replication and protein synthesis. In a preferred aspect of this embodiment, the tissue is rendered essentially acellular, the term "essentially" meaning having at least 70% fewer cells than the naturally occurring biological material. The extent of decellularization can be determined histochemically, for example, by staining the tissue with hematoxylin and eosin using standard techniques. Immunohistochemical staining can also be used, for example, to visualize cell specific markers such as smooth muscle actin and histocompatibility antigens—an absence of such markers being a further indication of decellularization.

In accordance with the present method, the biological tissue is, preferably, first washed in a solution of a bioburden reducing agent, such as an antibiotic. The tissue can then be decellularized immediately or it can be cryopreserved. Cryopreserved tissue is thawed prior to decellularization under conditions such that the cryoprotectant is eliminated and toxicity resulting therefrom thereby avoided. Appropriate thawing conditions are well known in the art. The tissue (fresh or thawed cryopreserved) is then placed in hypotonic solution in order to effect cell lysis. Appropriate solutions include water or a solution having a solute (eg a salt such as NaCl) concentration of up to 80 milliosmolar (for example, a 10-20 or 20-40 mM NaCl solution). Lysis can be effected, for example, at a temperature in the range of 30° C. to 40° C., preferably 37° C., advantageously in an atmosphere of 5% $CO_2$, for example, for about 4 to 24 hours. The tissue is then transferred to a nuclease solution (eg DNAase- and/or RNAase-containing) and incubated, for example, at a temperature in the range of about 30° C. to 40° C., preferably 37° C., advantageously in an atmosphere of 5% $CO_2$, for example, for about 4 to 24 hours. Subsequently, the tissue is transferred to a solution that can maintain tissue structural integrity, for example, a physiologically normal (isotonic) solution such as a cell culture medium, eg DMEM. Cell lysis can continue during maintenance of the tissue in the physiologically normal solution and thus the tissue can be removed from the lytic/nuclease solutions before 70% decellularization has been achieved.

Tissues that have been decellularized can be terminally sterilized using any of a variety of sterilants. For example, the tissue can be subjected to gamma irradiation, ethylene oxide, peracetic acid, β-propiolactone, povidone-iodine, or UV irradiation in the presence or absence of photosensitizers. Appropriate conditions for effecting terminal sterilization are well known in the art.

Biological tissues suitable for use in the present method include those appropriate for implantation into humans or animals. Tissues can be human or non-human (eg bovine, porcine or non-human primate) in origin. As indicated above, the tissues can be fresh or cryopreserved. In either case, the tissue is decellularized prior to any fixation. While the present invention is exemplified by reference to heart valve leaflets, the decellularization method is applicable to other tissues as well, including tendons, ligaments, facia, arteries, veins, diaphragm, pericardium, umbilical cords, dura mater or tympanic membranes.

Upon completion of decellularization, the biological tissue can be processed and/or fabricated as appropriate depending on the ultimate use of the tissue. Any fixation of the decellularized tissue can be effected using art-recognized techniques, including glutaraldehyde fixation. Unfixed tissue, however, can also be used. Unfixed tissue can be impregnated with any of a variety of agents including those that stimulate recellularization upon implantation of the decellularized tissue in vivo. Examples of such agents include growth factors, adhesion factors, such as glycosaminoglycans, and soluble extracellular matrix glycoproteins such as fibronectin, laminin, vitronectin, etc. Other agents that can be used include those that augment hemocompatability, thrombomodulators, and antibiotics. Appropriate impregnation techniques are known in the art. When the tissue is a heart valve, fabrication with a biological or non-biological stent can be effected using standard protocols.

Bioprostheses produced in accordance with the present invention can be used as replacements for defective tissues in mammals, particularly humans. Methods of effecting the replacement of, for example, heart valves, tendons, ligaments, vessels, etc., are well known in the art.

Tissue decellularized in accordance with the present invention is subject to less mineralization (eg calcification) in vivo than non-treated tissue. Decellularization also results in a tissue that is reduced in immunogenicity.

Certain aspects of the present invention are described in greater detail in the non-limiting Examples that follow. While the decellularization methodology of the present invention and that of U.S. Pat. No. 5,595,571 are distinct, it will be appreciated that certain details of that disclosure are equally applicable here, including source of biological tissues, methods of monitoring extent of decellularization and methods of processing and fabrication post decellularization. Accordingly, U.S. Pat. No. 5,595,571 is incorporated in its entirety by reference.

EXAMPLE I

Decellularization of Leaflets and Whole Values

The following solutions are utilized in the protocols that follow:

1M Tris pH 7.6: To 80 ml deionized water add 11.21 gm Tris, adjust pH to 7.6 with 1N NaOH and bring volume to 100 ml and store at 4° C.

1M $CaCl_2$: To 20 ml deionized water add 2.22 gm $CaCl_2$ and store at 4° C.

1M $MgCl_2$: To 10 ml deionized water add 2.033 gm $MgCl_2$ and store at 4° C.

DNAse I Solution: To 4.95 ml sterile water add 5 ml glycerol (final conc 50%), 20 mg DNAse I (Sigma D5025) (final conc 2 mg/ml), and 50 µl 1M $CaCl_2$ (final conc 5 mM). Aliquot 1 ml to chilled labeled 1.5 ml microfuge tubes and store at −20° C.

RNASe A Solution: To 10 ml sterile water add 100 mg RNAse A, and mix to dissolve. Aliquot 500 µl of solution to each of 20 prechilled 1.5 ml microfuge tubes and store at −20° C.

Nuclease Solution: To 93.66 ml sterile water, add 4.8 ml 1M Tris pH 7.6 (final 48 mM), 288 µl 1M $MgCl_2$ (final conc 2.88 mM), 96 µl 1M $CaCl_2$ (final conc 0.96 mM), filter sterilize using 0.2 micron filter, add 960 µl 2 mg/ml DNAse I (final conc 19.2 µg/ml) 192 µl 10 mg/ml RNAse A (final conc 19.2 µg/ml).

Decellularization of Leaflets

Day 1

A valve is removed from a liquid nitrogen freezer and submerged in a 37° C. water bath for approximately 15 min. Under sterile conditions, the valve is removed from the packaging and placed in a sterile 7 oz. specimen cup with approximately 50 ml of lactate-ringer 5% dextrose (LRD5) solution for 15 min. at room temperature. The valve is dissected by making a single cut down the commisure located between the left and right coronary arteries. The valve is laid open with the mitral valve leaflet up, the left coronary leaflet to the left, the right coronary leaflet to the right, and the non-coronary leaflet in the middle. The leaflets are dissected free of the valve as close to the conduit wall as possible and placed in separate labeled 15 ml conical centrifuge tubes filled with 10 ml LRD5 solution for 10 minutes at room temperature. The leaflets are moved to second labeled 15 ml conical centrifuge tubes filled with 10 ml LRD5 solution and allowed to stand for 10 minutes at room temperature. The leaflets then are moved to third labeled 15 ml conical centrifuge tubes filled with 10 ml sterile water and placed in an incubator at 37° C. 5% $CO_2$ for 2 hours. The leaflets are placed in 6-well culture plates and weighted down with sterile glass rings. 5 ml nuclease solution is added to each well and the leaflets incubated overnight at 37° C. 5% $CO_2$.

Day 2

The nuclease solution is removed and 5 ml of DMEM is added to each well and the leaflets are returned to the incubator.

Day 3-16

The medium is changed every other day for two weeks.

Alternative Procedure for Whole Valves

If valves have been cryopreserved, they are thawed and washed as above; if valves are fresh, they are washed once in 80 ml of LRD5 for 15 minutes in a 7 oz sterile specimen cup.

After the valve is washed, it is transferred to a 7 oz sterile specimen cup containing about 80 ml of sterile $H_2O$ and placed in the 37° C. 5% $CO_2$ incubator for 4 hours.

The valve is removed to a 7 oz sterile specimen cup containing about 80 ml nuclease solution and returned to the incubator overnight.

Day 2

The valve is removed to a 7 oz sterile specimen cup containing about 80 ml (ALT+) solution (containing netilmicin, 54 µg/ml;, lincomycin, 131 µg/ml; cefotaxime, 145 µg/ml; vancomycin, 109 µg/ml; rifampin, 65 µg/ml; fluconazole, 100 µg/ml; and amphotericin B, 84 µg/ml).

Day 3-16

The medium is changed every other day for two weeks using ALT+ solution for the first week and DMEM for the second.

The foregoing procedures are open culture procedures. Thus the specimen cup lids are loosened when placed in the incubator.

EXAMPLE II

Experimental Details:

Porcine heart valves. Porcine hearts were obtained from market weight pigs (>120 kg). After rinsing in sterile phosphate buffered saline, the hearts were field dissected (apex removed) and shipped at 4° C. in sterile PBS. All hearts arrived within 24 hr of animal slaughter. Aortic and pulmonary valves were dissected as roots. These tissues were subjected to a bioburden reduction step of incubation in a mixture of antibiotics and antimycotics for 48 hr at 48° C. The disinfected tissues were either cryopreserved (10% (v/v) DMSO and 10% (v/v) fetal bovine serum, −1° C./min) or were decellularized by a procedure involving treatment with hypotonic medium followed by digestion with a mixture of deoxyribonuclease I and ribonuclease A. After 12 days, the decellularized valves were either cryopreserved as above or chemically fixed in 0.35% (w/v) glutaraldehyde at 2 mmHg in phosphate buffered saline (pH 7.4) for a total of 7 days; the low pressure fixation ensures maintenance of the natural crimp of the collagen matrix. The fixed tissues were not cryopreserved, but were stored in 0.35% glutaraldehyde solution.

Prior to any examination (calcification, biomechanics, histology), the cryopreserved tissues were thawed rapidly to prevent ice-recrystallization by immersion of the packaged tissue in a 37° C. water bath. Cryopreservation medium was eluted from the thawed valves with 500 ml of lactated-Ringers solution containing 5% dextrose. The glutaraldehyde-fixed tissues were washed three times each with 200 ml of normal saline.

In vivo static calcification. Calcification of treated tissues was assessed in vivo by subdermal implantation in rats. Weanling male, Sprague-Dawley rats were obtained from Charles Rivers Laboratories. After one week equilibration, animals averaged 136±18 g in weight. The heart valves were dissected to provide aortic and pulmonary leaflets and vascular conduit sections, each 0.5 cm square. With the rats under ketamine and xylazine (10 mg/kg and 5 mg/kg, respectively, IP) anesthesia, and following preparation of a sterile field, 2 cm diameter pouches were formed in the dorsal subcubitae, four per animal, and sections of tissues inserted. Incisions were closed with stainless steel staples. The rats were allowed to recover and were then permitted free access to food and water. Tissue samples were recovered at 1, 2, and 4 months post-implantation for determination of calcium content.

Method for calcium determination in tissue samples. Recovered tissues were washed in sterile calcium and magnesium-free phosphate buffered saline, three times 10 ml each. Wet weight was measured, and after mincing, the pieces were dried overnight in a centrifugal evaporator (Savant Speed-Vac). After recording dry weight the tissues were digested in 10 ml of 25% (v/v) $HNO_3$ for at least 24 hr at 70° C. An aliquot of the digest solution was diluted 10-fold in 0.2 N HCl containing 1% (w/v) lanthanum nitrate. Finally, calcium content was measured using a Perkin-Elmer 300 atomic absorption spectrometer calibrated with a certified calcium standard from SPEX Plasma Standards (Cat. PLCA2-3Y. Response in this system was linear between 0.2-20 µg/ml.

Biomechanics testing. Aortic and pulmonary leaflets were die cut in the circumferential dimension to provide "dog-bone"-shaped specimens, 0.5 cm wide at midsubstance. Thickness of each sample was derived from the average of three measurements taken with a low mass pin attached to a conductance circuit and digital caliper. Leaflets were mounted in specially designed clamps with a standard gauge length of 1 cm. All testing was carried out with the tissue in Hank's balanced salt solution maintained at 37±2° C. Each specimen was preconditioned to a load of 150 g until successive load-elongation curves were superimposable (~20 cycles). The following measurements were then taken: 1) low-load elongation to derive stress-strain relationships while imposing up to 150 g load on the tissue at an extension rate of 10 mm/min, a rate which reflects previously reported studies of leaflet biomechanics (Leesson-Dietrich et al, J. Heart Valve Disease 4:88 (1995)); 2) examination of viscoelastic properties of the specimens in a stress-relaxation study (tissue elongated to a load of 150 g and following residual loads for up to 1000 sec)—both the % of initial load remaining at these time points as well as the rate of stress-relaxation (i.e., the slope of the percent stress remaining versus time) were determined; and 3) ultimate uniaxial tensile testing to tissue failure. At least 8 specimens of each tissue type were examined.

Histochemistry. Samples of fresh and explanted tissues were immersed in 10% sucrose solution for 4-18 hr at 4° C. After brief fixation in 10% formalin, the pieces were placed in molds and frozen in OCT using a liquid nitrogen bath. Cryosections, 6-10 µm thick, were cut using an IEC cryostat (Needham Heights, Mass.). Sections were then stained either with hematoxylin and eosin or stained specifically for calcium according to the method of von Kossa (Theory and Practice of Histological Techniques, edited by Bancroft and Stephens, Churchill Livingstone, Edinburgh (1990)). Sections were viewed and photographed using a Nikon Optiphot microscope.

Statistics. Statistical differences in the group means of biomechanical parameters was assessed by independent t-tests. A p value of 0.05 was chosen as the level of significant differences. Calcium data were analyzed according to ANOVA testing carried out with the statistical program for the IBM-PC, SPSS-PC.

Results

Biomechanics. Low load testing—extensibility and low modulus. The biomechanical properties of strips of aortic and pulmonary porcine heart valve leaflets were compared between fresh-cryopreserved and decellularized-cryopreserved tissues. Fresh aortic and pulmonary leaflets were found to have significant differences in extensibility; pulmonary leaflets had extension 2.3-fold greater than aortic leaflets (p<0.01)). However, the elastic modulus of these tissues were not different pre-decellularization (10.6±1.1 vs. 9.15±0.64, p=0.255, FIG. 1). With decellularization, the extensibility of the two leaflet type became indistinguishable (30.4±2.5 vs. 30.2±3.3, p=0.981). The elastic modulus of the aortic leaflets was unchanged by decellularization (p=ns (not significant)), as compared to the fresh tissue). In contrast, pulmonary leaflet tissues was markedly stiffened by decellularization, with the elastic modulus rising by 660%, (p=<0.05). As a result, the elastic modulus of decellularized pulmonary tissue was 550% greater than that of the decellularized aortic leaflet.

Figure 2:
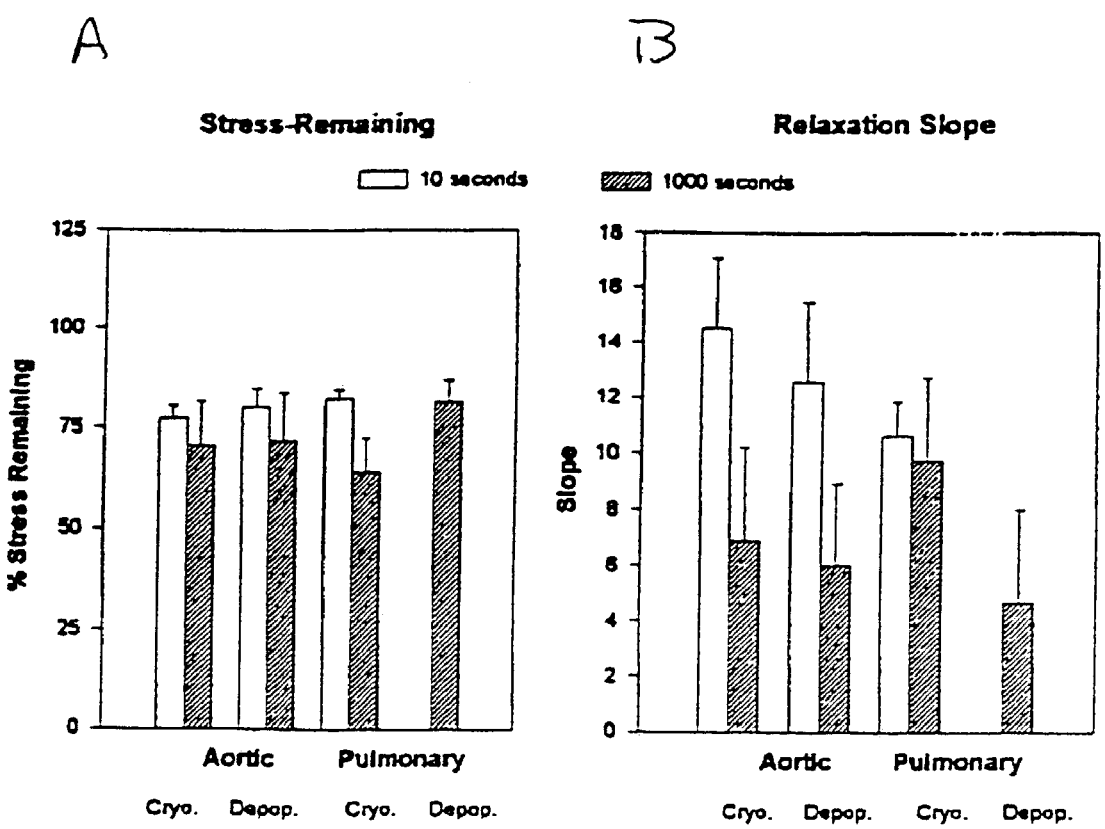
FIGS. 2A and B show the effect of decellularization on rates of stress-relaxation of aortic and pulmonary leaflets.

Stress-relaxation testing. The initial (10 sec) and the final (1,000 sec) rates of stress-relaxation for fresh aortic and pulmonary leaflets were comparable and not statistically different (p=0.103 and p=0.115, respectively, FIG. 2). For decellularized tissues, only the initial rate of stress-relaxation or aortic leaflets was obtained; this was no different from the fresh tissue value. The increased stiffening of the pulmonary leaflets with decellularization which was observed with low-load testing was reflected by a higher final level of stress remaining (increase from 64.1±2.18% to 81.5±2.5%). The relaxation slope for the pulmonary leaflets were reciprocally changed by decellularization, decreasing from 9.8±0.8 in the fresh tissue to 4.7±1.5 in the treated tissue.

Figure 3:
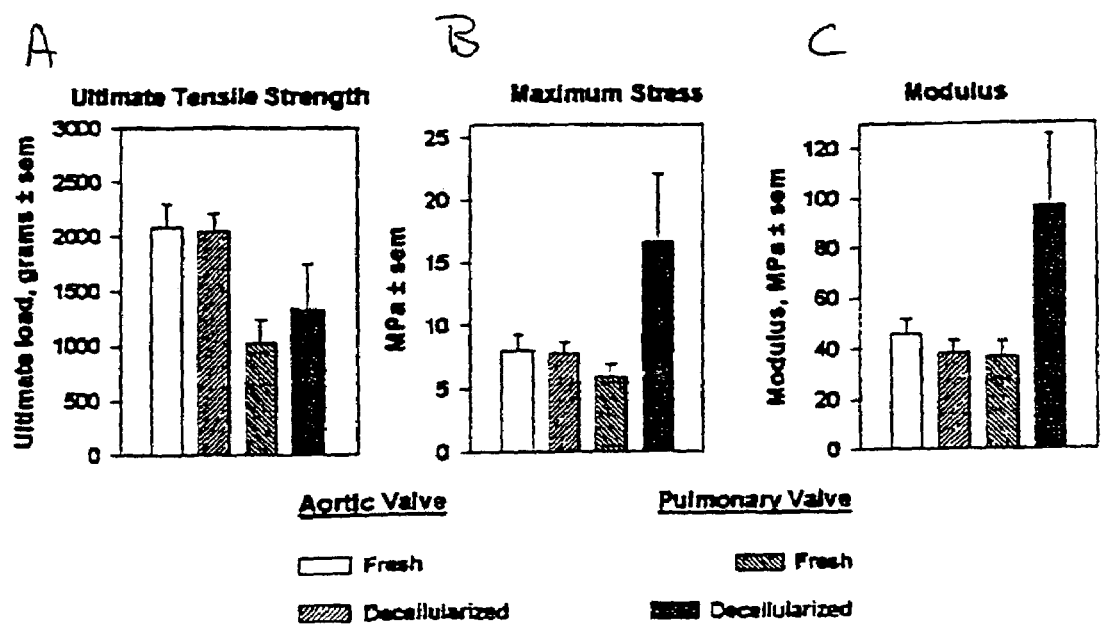
FIGS. 3A, B and C show the effect of decellularization on failure load, maximum stress and elastic modulus of aortic and pulmonary leaflets.

Ultimate tensile testing—failure load, maximum stress, and elastic modulus (FIG. 3). In fresh tissues the aortic leaflets failed a twice the load as did the pulmonary valve tissue (p<0.001). However, there was no statistical difference maximum stress at failure of the aortic and pulmonary leaflets (8.0±1.2 MPa vs. 6.0±0.9, p=0.202). As well, the moduli of the fresh leaflets were not statistically different (p=0.333).

Decellularized aortic leaflets failed at the same load and maximum stress as did the fresh tissue. The failure load of pulmonary leaflets rose slightly but not significantly, but there was almost a tripling of the stress at failure.

The stiffening of Pulmonary leaflets observed with load testing was again reflected when the tissue was loaded to failure. The modules of pulmonary leaflets taken to failure increased 2.6-fold after decellularization; in contrast, the elastic modules of the decellularized aortic leaflets declined slightly (45.5±6.2 MPa vs. 38,3±5.2 Mpa).

Tissue calcification. The kinetics of calcification of porcine heart valve tissues at 1, 2, and 4 months of implantation are presented in FIG. 4. Glutaraldehyde-fixed porcine pulmonary heart valve tissues appeared especially prone to calcify in the subdermal rat model. The pulmonary leaflets and vascular conduit calcified more rapidly than their aortic valve counterparts, the fixed pulmonary leaflets calcifying most rapidly of all tissues examined. Furthermore, glutaraldehyde-fixed pulmonary leaflets attained the highest tissue content of calcium over the four months of subcutaneous implantation. In general, the fixed vascular conduits calcified more slowly than the leaflets from the same valve type and the final calcium content was significantly lower (p<0.05 for both aortic and pulmonary valves) at 4 months.

The impact of depopulation on heart valve calcification seen as a slowing of the calcification of fixed or non-fixed tissue (pulmonary leaflet) or a plateauing of calcification after two months of implantation (aortic leaflet, aortic conduit, pulmonary artery). The plateau phenomenon was seen in either the unfixed tissues or in those which were decellularized prior to glutaraldehyde fixation. No statistically significant difference in the calcification of aortic conduit was found among the treatment groups over the 4 months of implantation. Calcification of decellularized aortic conduit proceeded more quickly than fixed tissue for the first 2 months of implant, and then leveled off while fixed conduit calcium content continued to rise. An attenuating effect on the increase in pulmonary artery calcium content was also observed relative to either fixed tissue group.

Aortic and pulmonary leaflets had somewhat different responses to decellularization. Decellularization of aortic leaflets with subsequent fixation resulted in lower calcium content (73±17 mg $Ca^{2+}$/g tissue) than aortic leaflets which were not fixed (121±8 mg/g, p<0.05). Although tissue was not available from the 4 month time point, in pulmonary leaflets, the decellularized tissue per se tended to have lower calcium content (152±5 vs. 101±34 mg/g at 2 months of implantation).

Histologic examinations. Areas of decellularized porcine aortic leaflet at 1 month can be shown free of endogenous cells within the tissue matrix as well as having no deposits. Since measured tissue calcium in this group was 60±14 mg/g, calcific deposits were found only in localized areas. When examined further using von Kossa's stain, such areas were evident. Within these areas calcium deposits appeared in association with nonspecific structures. In contrast, the early calcification of nondecellularized glutaraldehdye-fixed tissues was always associated with cell nuclei. The increasing extent of involvement of the leaflet tissue with time of implant is evident from a 1, 2, and 4 month sequence. The midsubstance of the leaflets calcified early, while the margins calcified later. In either the aortic or pulmonary valve vascular components, calcified areas typically remained at the periphery of the implant, and only infrequently did tissues show evidence of mineralization of the midsubstance of the implant.

All documents cited above are hereby incorporated in their entirety by reference.

One skilled in the art will appreciate from a reading of this disclosure that various changes in form and detail can be made without departing from the true scope of the invention.

What is claimed is:

1. A method of producing a bioprosthetic tissue consisting essentially of the of the steps of:
   i) washing a starting tissue selected from the group consisting of a heart valve, tendon, ligament, artery, vein, diaphragm, pericardium, fascia, dura mater and tympanic membrane with a bioburden reducing agent so that said starting tissue is disinfected,
   ii) subsequent to step (i), contacting said disinfected tissue with a hypotonic solution so that lysis of cells of said disinfected tissue is effected,
   iii) incubating the hypotonic solution-treated tissue resulting from step (ii) with at least one enzyme, wherein said at least one enzyme consists of at least one nuclease, so that nucleic acid associated with said cells lysed as a result of step (ii) is degraded, and
   iv) sterilizing the nuclease-treated tissue resulting from step (iii).

2. The method according to claim 1 wherein said method of production further consists essentially of, after step (iii), the step of contacting the tissue resulting from step (iii) with a physiologically isotonic solution.

3. The method according to claim 1 wherein said starting tissue is a human tissue.

4. The method according to claim 3 wherein said starting tissue is obtained from a human heart valve.

5. The method according to claim 1 wherein said tissue resulting from step (iii) is at least 70% decellularized.

6. The method according to claim 1 wherein said at least one enzyme consists of DNAase or RNAase.

7. The method according to claim 1 wherein said at least one enzyme consists of DNAase and RNAase.

8. The method according to claim 1 wherein said starting tissue is non-human tissue.

9. The method according to claim 1 wherein said bioburden reducing agent is an antibiotic or mixture of antibiotics.

10. The method according to claim 1 wherein said step (ii) is carried out at a temperature of between 30° to 40° C.

11. The method according to claim 1 wherein said method of production further consists essentially of, after step (i), the steps of cryopreserving said disinfected tissue and then thawing said cryopreserved, disinfected tissue.

12. The method according to claim 1 wherein, in step (ii), said hypotonic solution is water.

* * * * *